United States Patent
Bohus

(10) Patent No.: US 9,539,295 B2
(45) Date of Patent: Jan. 10, 2017

(54) CANNABIDIOL (CBD) ENRICHED ALCOHOL

(71) Applicant: Bradley Michael Bohus, Westerville, OH (US)

(72) Inventor: Bradley Michael Bohus, Westerville, OH (US)

( * ) Notice: Subject to any disclaimer, the term of this patent is extended or adjusted under 35 U.S.C. 154(b) by 0 days.

(21) Appl. No.: 14/959,849

(22) Filed: Dec. 4, 2015

(65) Prior Publication Data

US 2016/0158299 A1    Jun. 9, 2016

Related U.S. Application Data

(60) Provisional application No. 62/087,833, filed on Dec. 5, 2014.

(51) Int. Cl.
| | |
|---|---|
| *A01N 65/00* | (2009.01) |
| *A61K 36/185* | (2006.01) |
| *A61K 47/10* | (2006.01) |
| *A61K 9/00* | (2006.01) |

(52) U.S. Cl.
CPC ........... *A61K 36/185* (2013.01); *A61K 9/0095* (2013.01); *A61K 47/10* (2013.01)

(58) Field of Classification Search
CPC ..................................................... A61K 36/00
USPC ....................................................... 424/725
See application file for complete search history.

(56) References Cited

U.S. PATENT DOCUMENTS

| | | |
|---|---|---|
| 6,403,126 B1 | 6/2002 | Webster et al. |
| 6,630,507 B1 | 10/2003 | Hampson et al. |
| 7,399,872 B2 | 7/2008 | Webster et al. |
| 7,402,686 B2 | 7/2008 | Duchek |
| 7,622,140 B2 | 11/2009 | Whittle et al. |
| 7,923,558 B2 | 4/2011 | Arslantas et al. |
| 8,222,292 B2 | 7/2012 | Goskonda et al. |
| 8,227,627 B2 | 7/2012 | Stinchcomb et al. |
| 8,980,940 B2 | 3/2015 | Rossi et al. |
| 2006/0167283 A1 | 7/2006 | Flockhart et al. |
| 2011/0038958 A1 | 2/2011 | Kikuchi et al. |
| 2013/0245110 A1 | 9/2013 | Guy et al. |
| 2014/0302148 A1 | 10/2014 | Winnicki |

*Primary Examiner* — Michael Meller
(74) *Attorney, Agent, or Firm* — Roger A. Jackson

(57) ABSTRACT

A cannabinoid enriched alcohol composition for human consumption and method of manufacture for the composition are disclosed. The composition includes by weight about ninety-nine point nine-two percent (99.92%) ethanol in a liquid state and by weight about zero point zero eight percent (0.08%) cannabinoid in a liquid state. The composition is made by providing the ethanol in a liquid state and by providing the cannabinoid in the form of a cannabidiol oil in a liquid state, further a next step of combining the ethanol and the cannabidiol oil forming an initial mixture and agitating the initial mixture until the cannabidiol oil and the ethanol are in a substantially emulsified state with one another in a liquid state forming a completed mixture.

4 Claims, No Drawings

CANNABIDIOL (CBD) ENRICHED ALCOHOL

RELATED PATENT APPLICATION

This application claims the benefit of U.S. provisional patent application Ser. No. 62/087,833 filed on Dec. 5, 2014 by Bradley Michael Bohus of Columbus, Ohio, U.S.

FIELD OF THE INVENTION

The present invention generally relates to a composition that combines alcohol and a cannabinoid and further a method of making an alcohol and cannabinoid composition. More particularly the present invention composition utilizes a variety of consumable alcohols either singular or in combination with oil from industrial hemp plants being preferably in particular non-psychoactive cannabinoids such as cannabidiol.

DESCRIPTION OF THE RELATED ART

Looking at the prior art in this area, in U.S. Pat. No. 6,630,507 to Hampson et al., disclosed is a formulation for the antioxidant properties of cannabinoids for treating a wide variety of oxidation associated diseases for instance such as inflammatory and autoimmune diseases that can include stroke, trauma, Alzheimer's, Parkinson's, and HIV dementia. Thus in Hampson, utilizing non-psychoactive cannabinoids, such as cannabidiol are beneficial as they avoid the high toxicity that is encountered with psychoactive cannabinoids at high doses that are useful for the above mentioned conditions. In Hampson, the focus is upon permanent injury to the central nervous system, as the brain has high oxygen requirements and can sustain permanent damage if deprived of oxygen for only a few minutes, one aspect of brain oxygen deprivation is the production of glutamate which results in toxins being present that damage cellular structures, and thus if the glutamate toxicity can be reduced, then accordingly cellular structure damage can be reduced in the brain, wherein this process is known in the art, the problem is in that the brain being protected by the blood brain barrier does not give ready physical access to common anti-oxidants and anti-inflammatory agents for reducing glutamate toxicity. Thus, the goal for Hampson is the use of antioxidant drugs that are substantially free of psychoactive effects (allowing higher doses) and have good physical tissue penetration, especially at the blood brain barrier, for reducing the aforementioned glutamate toxins and therefore brain damage from lack of oxygen.

Further, in the prior art in U.S. Pat. No. 7,402,686 to Duchek disclosed is a composition that is highly stable in crystalline form at room temperature for storing purified THC as a cannabinoid compound. In Duchek the cannabinoid is mixed with an aryl sulfonyl halide plus a tertiary amine that are all mixed in an organic solvent until completion, wherein the solvent is then removed leaving an oil that can then be crystallized for indefinite storage. Thus, in Duchek then the crystallized cannabinoid esters can be hydrolyzed to recover the pure cannabinoid by base hydrolysis.

Continuing, in the prior art in U.S. Pat. No. 7,622,140 to Whittle et al., disclosed is a process and apparatus for extracting natural products from plant material for example by using hot gas. Typically in plant based products the desired active constituent is present in the native plant material is in a small percentage, wherein a majority of the native plant material is biomass. According to Whittle, the problem with any extraction process is firstly to not damage or undesirably alter the desired constituent (from temperature/agitation, etc.) and secondarily for the extraction process for the solutions used themselves to not leave their own undesirable elements as artifacts of the extraction process. Thus in Whittle, ideally the extraction process will try to extract the desired constituent without alteration or added residual elements, wherein the process in Whittle has a distillation step with the natural product exposed to a hot gas for a vapor to be formed that contains the constituent with the vapor condensed to form the desired extract particularly in the extraction of cannabinoid-rich factions from cannabis plant material. In Whittle, the preferred hot gas is a non-oxidizing type such as dry steam that is well above its condensation temperature thus not having any water vapor present.

Continuing in the prior art in U.S. Pat. No. 6,403,126 to Webster et al., disclosed is a cannabinoid extraction method that utilizes ground chaff from the plant that is separated from the plant seeds, wherein an organic solvent is used in a chromatographic column to fractionate cannabinoids, cannflavins, and essential oils. Webster further discloses using industrial hemp as the plant and drying the chaff prior to extraction. Next, in the prior art in U.S. Pat. No. 7,235,584 to Garzon et al., disclosed are compositions for non-psychotropic cannabinoids, specifically for treating inflammatory disorders in minimizing damage to the central nervous system being similar to Hampson.

Next, in the prior art in U.S. Pat. No. 7,399,872 to Webster et al., disclosed is a cannabinoid purification method that converts cannabidiol to tetrahydrocannabinol that utilizes an organic solvent to separate the mixture into an aqueous phase and an organic phase, then removing the organic phase and washing the organic layer with water and eluting tetrahydrocannabinol having purity greater than 97%. Following onward, in the prior art in U.S. Pat. No. 7,449,589 to Geiser et al., disclosed is a process similar to '872 Webster for purification of tetrahydrocannabinol using a chromatographic technique with a mixture of carbon dioxide and a liquid solvent such as alcohol for a "mobile phase" and a derivatized polysaccharide immobilized on a substrate that can be a ceramic for a "stationary phase". Geiser has the mobile phase pass through the stationary phase to produce at least one gram of the separated tetrahydrocannabinol within a time period of a day.

Further in the prior art in U.S. Pat. No. 7,923,558 to Arslantas et al., discloses yet another method for obtaining pure tetrahydrocannabinol, wherein Arslantas uses a solvent to create a crystallized form from the raw plant product, being similar to Duchek in utilizing crystallization. In Arslantas, the negatives of chromatographic separation are discussed that requires a large volume of solvent, wherein the solvent must later be removed at high cost, further, use of distillation is not ideal either as the THC constituents have boiling points that are close to one another, thus making efficient distillation difficult and the high heat requirements for the high boiling temperatures of about 150 degrees Celsius at 0.02 Torr (being basically a vacuum), thus creating the need for special equipment that would discourage the use of chromatographic separation.

Next, in the prior art in U.S. Pat. No. 8,222,292 to Goskonda et al., disclosed are liquid cannabinoid formulations that are for oral applications that are aqueous based that comprise water, alcohol, and propylene glycol that is stable at room temperature for application to medicinal purposes. Continuing, in the prior art in U.S. Pat. No. 8,227,627 to Stinchcomb et al., disclosed are compositions of tetrahydrocannabinol and methods of using the same, especially for transdermal delivery of pharmaceutically active agents. Stinchcomb, indicates that THC is highly hydrophobic in nature making it poorly absorbed through skin, thus THC compositions need to be developed that use the skins natural process for enzymes that can metabolize pharmaceutical agents which pass through the skin, however, desirably not being absorbed into overall circulation. Stinchcomb, cites the composition including an ester, a carbonate, and a phosphate that present a suitable bio-labile linking structure with moieties that can be selected to control the rate and extent of absorption.

Moving onward in the prior art in U.S. Pat. No. 8,980,940 to Rossi et al., discloses cannabinoid compositions and methods for making and storing them, the composition includes cannabinoid, an acid, and a pharmaceutically suitable solvent that achieves room temperature stability for over 24 months, wherein the acid improves the stability and the solvent enhances the solubility of the acid which helps the acid stabilize the cannabinoid. Rossi prefers the solvent to be an alcohol wherein the solvent is partially evaporated while the acid for instance as citric acid is added with an oil for instance a sesame oil that is added forming a pharmaceutical dosage. Rossi discloses typical weight percentages of the constituents as being for the solvent about 0.001% to 15%, for the oil at least about 90%, and enough acid to be sufficiently soluble in the solvent. Rossi indicates preferences on purity by weight at 0.5% of cannabinol with no more than 2% THC, and no more than about 2.5% total impurities.

Next, in the prior art in United States Patent Application Publication Number 2011/0038958 to Kikuchi et al., discloses the use of cannabinoids in combination with an anti-psychotic medicament for treatment of psychosis as a way to reduce the undesirable side effects of the typical anti-psychotic medicament. Further, in the prior art in United States Patent Application Publication Number 2014/0302148 to Winnicki, disclosed are cannabinoid formulations for pharmaceutical applications that particularly deal with the poor absorption of cannabinoids in oral administrated form due to the hydrophobic nature of cannabinoids from the poor dissolution of cannabinoids in the aqueous environment in the gastrointestinal tract. Thus, Winnicki discloses an aqueous micelle suspension of cannabinoids that do not include phospholipids and cholesterol, wherein the micelle diameter size is between 50-1000 nm for improving fat/oil solubility in solution. The basic process in Winnicki is to dissolve the cannabinoid in ethanol, then injecting the Cannabinoid and ethanol solution into distilled water to obtain the micelle Cannabinoid aqueous solution, and finally removing the ethanol from the solution to obtain the aqueous micelle suspension of a cannabinoid not having phospholipids, cholesterol, and oils under immersion microscopy.

Continuing, in the prior art in United States Patent Application Publication Number 2006/0167283 to Flockhart et al., discloses a method of preparing cannabidiol from plant material wherein the resultant cannabidiol having a chromatographic purity greater than 95%. Flockhart utilizes the crystalline form of CBD from plant material similar to Arslantas and Duchek who also use the crystalline form of CBD. Flockhart starts with a cannabidiol containing extract of the plant material, then dissolving the extract in a solvent (that can be alcohol) to form a solution, removing the insoluble material via filtration from the solution, and then evaporating the solvent via rotary evaporation to obtain substantially pure cannabidiol in crystalline form.

Further, in the prior art in United States Patent Application Publication Number 2013/0245110 to Guy et al., discloses use for cannabinoids in the manufacture of pharmaceutical formulations, particularly in reducing cholesterol, cannabinoid salts that are pharmaceutically acceptable that refer to salts or esters prepared from non-toxic bases or acids are acceptable. One embodiment disclosed by Guy is to contact the plant material with a hot gas bring greater than 100 degrees celsius that is sufficient to volatilize one or more cannabinoids to form a vapor that can be condensed to form an extract.

What is needed is a composition that helps to mitigate the negative effects of alcohol consumption upon the human consumer, these negative effects can include but are not limited to nausea, vomiting, headaches, impaired sensory and motor function, slowed cognition, stupefaction, unconsciousness, nervous system depressant, also alcohol can accelerate skin problems, asthma, and other problems related to the release of histamine for certain individuals reaction to alcohol. Cannabidiol (CBD) or as termed one of the non-psychotropic cannabinoids has been shown to help with alcohol tolerance, attenuation of; nausea, vomiting, gastrointestinal tract distress, and headaches, plus has anti-oxidant properties in humans, and further helps to ward off anxiety and depression. Thus, producing a human consumable drink that combines ethanol and CBD would act to allow the mildly psychoactive effects of euphoria and relaxation of moderate amounts of ethanol consumption, wherein the CBD would act to lessen the negative effects of ethanol consumption primarily being headache, nausea, and gastrointestinal tract distress.

SUMMARY OF INVENTION

Broadly, the present invention is of a cannabinoid enriched alcohol composition for human consumption and method of manufacture for the composition. The composition includes by weight about ninety-nine point nine-two percent (99.92%) ethanol in a liquid state and by weight about zero point zero eight percent (0.08%) cannabinoid in a liquid state. The composition is made by providing the ethanol in a liquid state and by providing the cannabinoid in the form of a cannabidiol oil in a liquid state, further a next step of combining the ethanol and the cannabidiol oil forming an initial mixture and agitating the initial mixture until the cannabidiol oil and the ethanol are in a substantially emulsified state with one another in a liquid state forming a completed mixture.

These and other objects of the present invention will become more readily appreciated and understood from a consideration of the following detailed description of the exemplary embodiments of the present invention.

DEFINITIONS

AGITATION 50—is when a velocity is created within the mixture 125 via passing a blade through the mixture 125 at a velocity greater that the mixture itself or alternatively via imparting movement to the mixture container at a velocity greater that the mixture itself.

ALCOHOL 55—preferably ethanol or ethyl alcohol in a liquid state, with a melting point of about negative (−) one hundred fourteen (114) degrees celsius and above.

CANNABIDIOL 60—(CBD) being the non-psychotropic cannabis constituent, is preferably derived from hemp in a liquid state, with a melting point of about sixty-six (66) degrees celsius and above. Hemp being defined as having less than about zero point three (0.3) percent % THC. Cannabidiol is a non-psychoactive cannabinoid that helps to avoid toxicity that is encountered with psychoactive cannabinoids. There are numerous cannabinoids that have been isolated from the cannabis plant.

CANNABIDIOL OIL 65—(CBD OIL) is where cannabidiol is dissolved in a medium of a human consumable oil that allows for varying percentages of cannabidiol concentration by weight within the oil, the oil typically is a byproduct of cannabidiol extraction from usually an industrial hemp plant being hemp oil extracts and fatty acids. Thus, the typical purity by weight of cannabidiol 60 to the oil of cannabidiol Oil 65 is about five (5) to fifty (50) percent.

CANNABINOIDS 70—are a group of chemical compounds that act upon the cannabinoid receptors in cells that are primarily in the brain which can include cannabinol, THC, or cannabidiol that is found in cannabis saliva (Marijuana) in the form of a phytocannabinoid (termed tetrahydrocannabinol or THC) being the psychoactive compound of cannabis or in the form of a synthetic cannabinoid. Two of the cannabinoids defined here are CBD 60 and CBN 75. Thus cannabinoids are the genus and CBD 60 and CBN 75 are some of the species of the genus of the cannabinoids.

CANNABINOL 75—(CBN) is the primary product of THC 135 degradation with little of this existing in a fresh cannabis plant, the aforementioned THC degradation is caused primarily from THC exposure to light and air over time, CBN is only mildly psychoactive.

CANNABIS PLANT 80—there are two major variants of the cannabis plant, the first is for Hemp and the second is for THC 135, wherein for the hemp variant the cannabis plants are tall growing (stalk focused with minimal leaves) and contain a lower content of THC 135, typically being in the range of about point zero five percent (0.05) % to one percent (1) % THC levels and the THC 135 variant of cannabis plants are lower growing (with maximum number of leaves) and have a higher THC content, typically being in the range of about five percent (5) % to thirty percent (30) % THC 135 levels.

CANNABIS PLANT (HEMP) 85—tall growing and having long fibrous stalks with few number of leaves and buds grown for hemp oil, wax, resin, hemp seed food, animal feed, cloth, and rope having low THC 135 content typically being in the range of about point zero five percent (0.05) % to one percent (1) % THC 135 levels. Note that CBD OIL 65 can be extracted from hemp plants with the resulting low THC 135 levels.

CANNABIS PLANT (MARIJUANA) 90—low growing and bushy with large number of leaves and buds grown for high THC 135 content typically being in the range of about five percent (5) % to thirty percent (30) % THC 135 levels. Note that CBD OIL 65 can be extracted from marijuana plants with the resulting high THC 135 levels.

CAVITATION 95—the formation of a gas pocket within a liquid caused by the rapid movement of a blade through a liquid, wherein the rapid blade movement causes a local pressure reduction in the liquid that results in a local liquid phase change from liquid to gas causing ineffective agitation and potential blade damage.

HEMP 100—products of the Hemp variant cannabis plant that include fiber, oil, and seed.

HOMOGENUS MIXTURE 105—as between the alcohol 55 and the cannabidiol 60 is defined as when the cannabidiol oil 65 is fully or partially emulsified within the alcohol 55 or in other words when the cannabidiol oil 65 is diffused in the alcohol 55.

PLANT BASED 110—extracts such as CBD 60, CBN 75, or THC 135 that are derived from cannabis plants.

PROOF OF ALCOHOL 115—an 18th century measurement of alcohol content of a spirit, wherein British sailors received part of their pay in Rum, and as a test of the alcohol content, gunpowder was floated on the Rum and tested to see if it would ignite, if it ignited the Rum was at least 57.15% alcohol (measured as Alcohol by Volume or ABV) if it didn't ignite then the Rum was less that 57.15% ABV, thus 57.15% ABV was deemed "100 Proof". This results in the ABV equaling the "Proof Number" times (4/7), thus; 150 Proof times (4/7) equals 85.71% ABV.

PSYCHOACTIVE 120—means cannabinoid brain receptor mediated psychoactivity that includes effects of euphoria, lightheadedness, reduced motor skills, and memory impairment. Psychoactivity does not include non-cannabinoid receptor mediated effects such as the anxiolytic effect of CBD 60, being generally decreased subjective anxiety and increased mental sedation, thus differentiating the psychological effects of THC 135 versus CBD 60.

COMPOSITION 125—the combined alcohol 55 and the cannabinoid 70 that is preferably in the form of the cannabidiol oil 65 that has an initial mixture and a final completed mixture.

SYNTHETIC BASED 130—Chemical constructions such as CBD, CBN, or THC that are not derived from cannabis plants. However, the chemical construction and effect upon the user can be different in a negative way than plant based extractions of CBD 60, CBN 75, or THC 135.

TETRAHYDROCANNABINOL 135—(THC) is the principal psychoactive constituent or cannabinoid of cannabis plants.

DETAILED DESCRIPTION

Broadly, the present invention is of a cannabinoid 70 enriched alcohol 55 composition for human consumption and method of manufacture for the composition 125. The composition 125 preferably includes by weight about ninety-nine point nine-two percent (99.92%) ethanol 55 in a liquid state and by weight about zero point zero eight percent (0.08%) cannabinoid 70 in a liquid state. The composition 125 is made by providing the ethanol 55 in a liquid state and by providing the cannabinoid 70 preferably in the form of a cannabidiol oil 65 in a liquid state, further a next step of combining the ethanol 55 and the cannabidiol oil 65 forming an initial mixture 125 and agitating 50 the initial mixture 125 until the cannabidiol oil 65 and the ethanol 55 are in a substantially emulsified state 105 with one another in a liquid state forming a completed mixture 125.

As an option for the composition 125, the cannabinoid 70 is preferably a cannabidiol oil 65, however, other cannabinoids 70 could also be used in the composition 125. Further, for the composition 125, the cannabinoid 70 can alternatively be selected from the group consisting of plant based 110, synthetic based 130, and/or a combination of plant 110 plus synthetic 130 based, in addition, for the composition 125, the cannabidiol oil 65 can also alternatively be selected from the group consisting of plant based 110, synthetic based 130, and/or a combination of plant 110 plus synthetic 130 based.

Another option for the composition 125 is in the weight percentage mixture of the ethanol 55 that can be up to about ninety-nine point nine-five percent (99.95%) by weight and the cannabidiol 60 about zero point zero five percent (0.05%) by weight. Note, also that a further option for the composition 125 is in the weight percentage mixture of the ethanol 55 can be up to about ninety-nine point nine-five percent (99.95%) by weight and the cannabinoid 70 about zero point zero five percent (0.05%) by weight.

Alternatively, for the composition 125, the cannabinoid 70 or the cannabidiol oil 65 can be non-psychoactive 120. Further, as an option for the composition 125, the cannabinoid 70 or the cannabidiol oil 65 can be derived from an industrial hemp plant.

Also, optionally for the composition 125, the cannabidiol oil 65 is preferably a cannabidiol oil 65 that has about a twenty-six percent (26%) by weight cannabidiol 60 content. Note that for the percent by weight of cannabidiol 60 content in the oil 65, the aforementioned percentages by weight as between the ethanol 55 and the cannabinoid 70 or the cannabidiol oil 65 refer to the actual pure cannabidiol 60 (or other pure cannabinoid 70) do not count the oil or other medium that the pure cannabidiol 60 or other pure cannabinoid 70 is processed in, so in other words for example if the cannabidiol oil 65 was a high purity ratio of pure cannabidiol 60 to the oil 65 content then a smaller amount of oil 65 would used and conversely if the cannabidiol oil 65 was a low purity ratio of pure cannabidiol 60 to the oil 65 content then a larger amount of oil 65 would used for the same percentages of the composition 125 in the weight percentage mixture of the ethanol 55 and either the cannabinoid 70 or the cannabidiol 60.

Another option, for the composition 125, the cannabidiol oil 65 preferably has no more than zero point three percent (0.3%) of tetrahydrocannabinol (THC) 135 content to reduce the psychoactive 120 effect. An additional option for the composition 125, the ethanol 55 is preferably an ethyl alcohol 55 and further as an option the ethyl alcohol 55 preferably has a proof 115 greater than 100, and continuing as an option the ethyl alcohol 55 is further preferably a clear vodka at 151 proof 115, or any suitable equivalent.

METHOD OF MAKING

A method of making a cannabidiol 60 enriched alcohol 55 composition for human consumption is disclosed, wherein the method includes the steps of firstly providing the ethanol 55 in a liquid state and a second step of providing the cannabidiol oil 65 in a liquid state. Subsequently a third step of combining the ethanol 55 and the cannabidiol oil 65 forming an initial mixture 125 and a fourth step of agitating 50 the initial mixture 125 until the cannabidiol oil 65 and the ethanol 55 are in a substantially emulsified state 105 with one another in a liquid state forming the completed mixture 125.

As an option for the method of making the cannabidiol 60 enriched alcohol 55 composition 125, an added optional fifth step of heating the initial mixture 125 in a range of about seventy degrees Fahrenheit (70° F.) to less than one-hundred seventy degrees Fahrenheit (170° F.) to further enhance the emulsified state 105 of the completed mixture 125. Further, on the optional fifth heating step it can be done either before, during, or after the fourth agitating step. A further optional refinement on the fifth step of heating the initial mixture 125 is to preferably narrow the temperature range to a range of about one-hundred degrees Fahrenheit (100° F.) to one-hundred sixty-five degrees Fahrenheit (165° F.).

Another option, for the method of making the cannabidiol 60 enriched alcohol 55 composition 125, wherein the initial mixture 125 can be placed in a vacuum that is below atmospheric pressure to further enhance the emulsified state 105 of the completed mixture, 125 by dropping the required fifth step heating temperature if desired or via adding agitation 50 via boiling of either the cannabidiol oil 65 or the ethanol 55 due to the vacuum.

A further option for the method of making the cannabidiol 60 enriched alcohol 55 composition 125, is that the fourth agitating 50 step can be accomplished by stifling at a velocity in a range of at least about an inch per second up to a velocity wherein cavitation 95 would occur in the initial mixture 125. In addition, optionally for the fourth 50 agitating 50 step the stifling is preferably a time period of at least about twenty (20) minutes.

A subsequent option for the method of making the cannabidiol 60 enriched alcohol 55 composition 125, wherein on the fourth agitating 50 step can be accomplished by engaging a container wherein the initial mixture 125 is disposed within the container, wherein the container is moved in an oscillatory motion being at least about one (1) cycle per second with a minimal total cycle amplitude that displaces at least about five (5) percent of a volume of the container. Thus the oscillatory motion total cycle amplitude is measured via the volumetric displacement of the container as against an external environment, wherein the container volumetric displacement from oscillatory motion has to equal at least about five percent of the container volume. A subsequent option for the method of making the cannabidiol 60 enriched alcohol 55 composition 125, wherein on the fourth agitating 50 step oscillatory motion is preferably done for a time period of at least about twenty (20) minutes.

CONCLUSION

Accordingly, the present invention of a CANNABIDIOL (CBD) ENRICHED ALCOHOL composition and method of making has been described with some degree of particularity directed to the embodiments of the present invention. It should be appreciated, though; that the present invention is defined by the following claims construed in light of the prior art so modifications or changes may be made to the exemplary embodiments of the present invention without departing from the inventive concepts contained therein.

The invention claimed is:

1. A cannabidiol enriched vodka composition for human consumption wherein the cannabidiol lessens the negative effects of vodka consumption by the human wherein the negative effects are headache, nausea, and gastrointestinal tract distress, said composition consisting essentially of:
   (a) about 99.92% vodka in a liquid state; and
   (b) about 0.08% synthesized liquid cannabidiol.

2. The cannabidiol enriched vodka composition for human consumption of claim 1, wherein said cannabidiol is non-psychoactive.

3. The cannabidiol enriched vodka composition for human consumption of claim 1, wherein said vodka has a proof greater than 100.

4. The cannabidiol enriched vodka composition for human consumption of claim 1, wherein said vodka is a clear vodka at 151 proof.

* * * * *